United States Patent [19]

Damon, II

[11] Patent Number: 4,588,715

[45] Date of Patent: May 13, 1986

[54] HEPTENOIC ACID DERIVATIVES

[75] Inventor: Robert E. Damon, II, Wharton, N.J.

[73] Assignee: Sandoz, Inc., E. Hanover, N.J.

[21] Appl. No.: 616,720

[22] Filed: Jun. 4, 1984

[51] Int. Cl.[4] .................. C07F 7/08; A61K 31/695
[52] U.S. Cl. .................................. 514/63; 549/214;
549/292; 556/441
[58] Field of Search ................ 549/214, 292; 556/441;
424/184; 560/56; 514/63

[56] References Cited

U.S. PATENT DOCUMENTS

| | | | |
|---|---|---|---|
| 4,000,265 | 12/1976 | Quilichini | 424/184 |
| 4,255,444 | 3/1981 | Oka et al. | 549/292 |
| 4,262,013 | 4/1981 | Mistui et al. | 549/292 |
| 4,293,496 | 10/1981 | Willard | 549/292 |
| 4,361,515 | 11/1982 | Terahara et al. | 549/292 |
| 4,375,475 | 3/1983 | Willard et al. | 549/292 |
| 4,420,475 | 12/1983 | Damon, II | 424/184 |
| 4,472,426 | 9/1984 | Hoffman et al. | 549/292 |

FOREIGN PATENT DOCUMENTS 7713317  5/1979  France .................. 424/184

*Primary Examiner*—Alton D. Rollins
*Assistant Examiner*—D. L. Dinner
*Attorney, Agent, or Firm*—Gerald D. Sharkin; Richard E. Vila; Frederick H. Weinfeldt

[57] ABSTRACT

Compounds of the formula

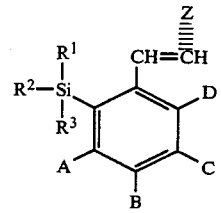

wherein $R^1$, $R^2$ and $R^3$ are alkyl or aryl groups, A, B, C and D are non-reactive substituents or two are joined to form an additional ring, and Z is either of the formula Z':

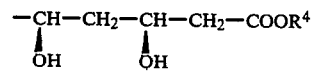

wherein $R^4$ is H, lower alkyl or a cation; or a -6-oxotetrahydropyran-2-yl ring of the formula Z":

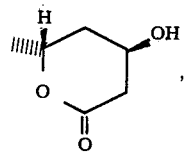

e.g. 4-hydroxy-6-{2-[2-(methyldiphenylsilyl)phenyl]ethenyl]ethyenyl}-tetrahydro-2H-pyran-2-one, (trans, trans). The compounds inhibit cholesterol biosynthesis and are useful as anti-atherosclerotic agents.

22 Claims, No Drawings

HEPTENOIC ACID DERIVATIVES

This invention relates to organic compounds, and more specifically to tetrahydropyran-2-ones having 6-olefinic substituents and to 7-substituted-hept-6-enoic acid derivatives, to pharmaceutical compositions containing such compounds, and to the use of such compounds, as well as to intermediates in the preparation of such compounds.

Final compounds of this invention are novel trans-olefins of the formula I:

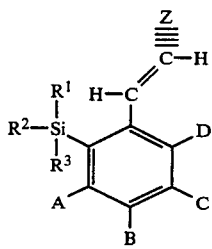

wherein each of $R^1$, $R^2$ and $R^3$ is independently, alkyl having from 1 to 4 carbon atoms; or phenyl which may be unsubstituted or substituted either by one or two alkyl or alkoxy groups having from 1 to 3 carbon atoms, or chloro; or by one fluoro, bromo or trifluoromethyl substituent;

A is a hydrogen atom or alkyl having from 1 to 3 carbon atoms, e.g. methyl;

B is a hydrogen atom; lower alkyl or alkoxy; halo, trifluoromethyl; or phenyl, benzyl, or benzyloxy, wherein the aromatic portion may be unsubstituted, or substituted by up to two groups, one of which may be fluoro, bromo or trifluoromethyl; or one or two of which may be lower alkyl or alkoxy, or chloro;

C is a hydrogen atom, lower alkyl or alkoxy, halo, or trifluoro methyl; and

D is a hydrogen atom, lower alkyl or alkoxy, halo or trifluoromethyl;

and any of A+B, B+C, or C+D may constitute a 4 carbon radical of the formula R°; which is either R°¹: —CH=CH—CH=CH—; or R°²: —(CH$_2$)$_4$—; to form a ring which is substituted by Q which is hydrogen; halo, or lower alkyl or alkoxy; and Z is a radical of the formula Z':

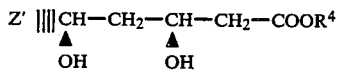

a radical of the formula Z":

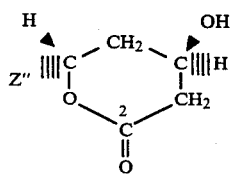

wherein $R^4$ is hydrogen, $C_{1-4}$alkyl, and benzyl; or M; wherein M is a pharmaceutically acceptable cation provided that there be no more than one trifluoromethyl group, and no more than two bromo substituents present on the molecule.

In the above definitions, unless otherwise defined, the term "halo" is intended to include fluoro, chloro, and bromo, and lower alkyl or alkoxy is intended to include those having from 1 to 4 carbon atoms. Where A+B, B+C or C+D constitute the radical R°, then the aromatic nucleus has the structure:

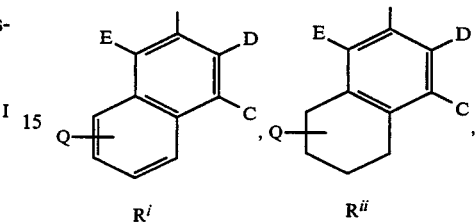

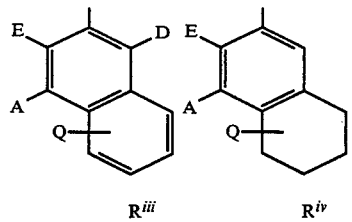

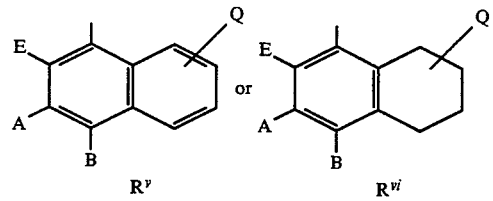

wherein A, B, C, D, and Q are as defined above, and E is the radical of the formula:

wherein $R^1$, $R^2$ and $R^3$ are as defined above.

Additional embodiments of this invention are processes for and intermediates in the synthesis of compounds I, the use of compounds I for inhibiting cholesterol biosynthesis and lowering the blood cholesterol level and, therefore, in the treatment of hyperlipoproteinemia and atherosclerosis, and pharmaceutical compositions for each use.

Compounds I may be viewed as consisting of four classes, depending on the nature of Z:

I', where Z=Z' and $R^4$ is $R^{4'}$, i.e. the same as $R^4$ when it is alkyl or benzyl;

I", where Z=Z' and $R^4$ is H;

$I^s$ where Z=Z' and $R^4$ is M as defined above; and

I''' where Z=Z".

The preparation of compounds III via method (a) is conveniently represented in Reaction Scheme A, below, and the preparation of compounds I from compounds III is conveniently represented in Reaction Scheme B, below, wherein A, B, C, D, E and $R^{4'}$ are as defined above, and $R^5$ is alkyl having from 1 to 3 carbon atoms, preferably ethyl, and $Z^1$ is chloro or bromo.

The preparation of compounds I by the method (Steps (a) to (m)) shown in Reaction Schemes A and B is hereinafter referred to as method (a).
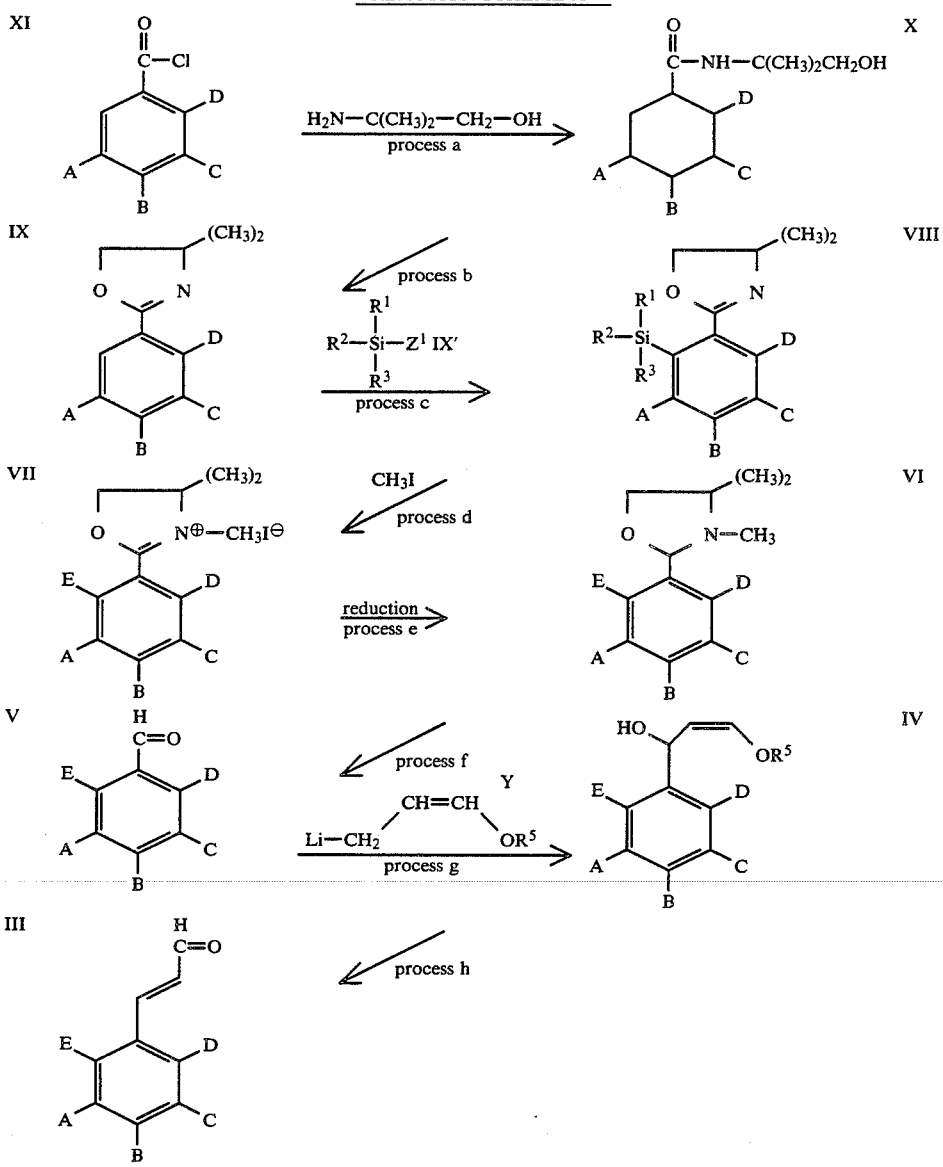
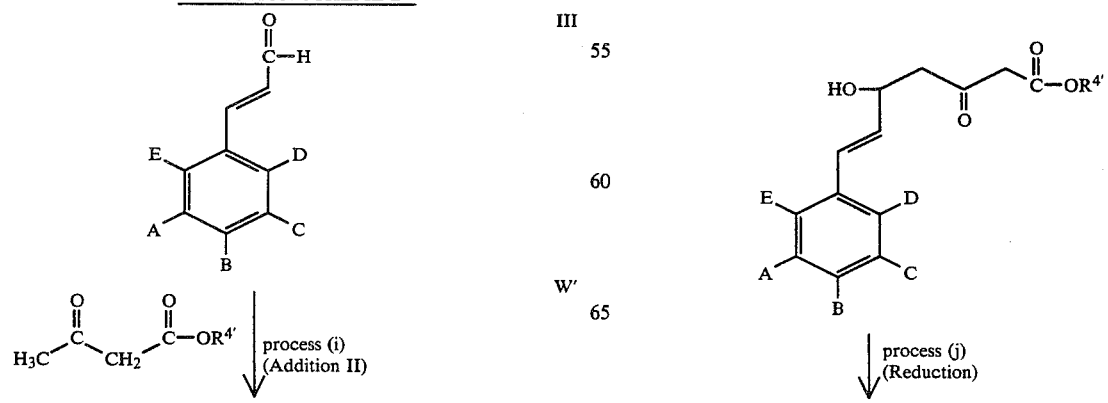

-continued
REACTION SCHEME B

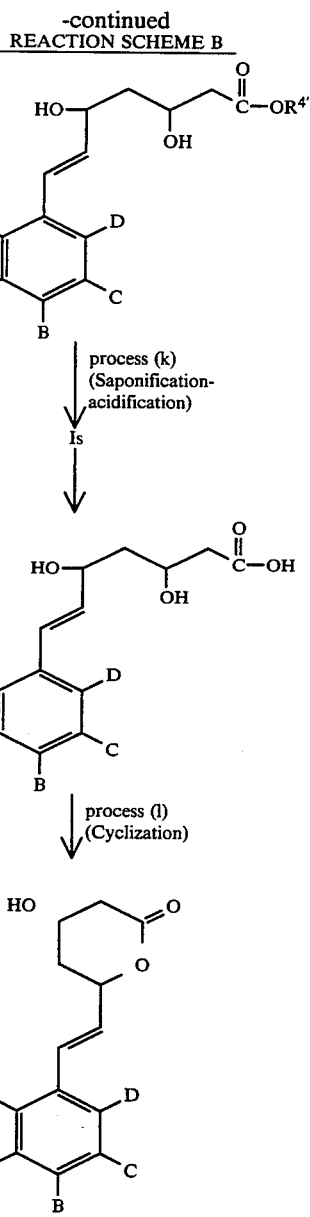

process (k)
(Saponification-acidification)

process (m)

process (l)
(Cyclization)

With respect to the processes represented in Reaction Schemes A and B, process (a) is an acylation reaction which may be carried out in the conventional manner, for such reactions, for example 2-amino-2-methylpropanol may be reacted with an acyl chloride of formula XI at moderate temperatures, e.g. from about −5° to 20° C., preferably at about 0° C., in an inert organic medium, e.g. a chlorinated lower alkane, such as methylene chloride. The reaction may be advantageously carried out in the presence of an acid receptor, or an excess of the amino alcohol may be included in the reaction mixture for that purpose.

In process (b) cyclization to form an oxazoline ring bearing product (a compound IX) may be carried out in the presence of a thionyl halide, preferably thionyl chloride, at moderate temperatures, e.g. from about 15° to 50° C., preferably by slowly adding the thionyl chloride to a compound X so that ambient room temperatures, e.g. 20° to 30° C., are maintained. If desired an inert organic solvent, e.g. a chlorinated lower alkane may be employed, but preferably a large excess of thionyl chloride is used as reaction medium. The hydrochloride form of the resulting compound IX is formed, from which a compound IX in free form is liberated by neutralizing with base, e.g. dilute aqueous sodium hydroxide, at moderate temperatures, e.g. at room temperature, and recovering the free product by extraction, e.g. with ether, and recovered.

The process (c) is carried out in two steps. First, a lithium salt of a compound IX is prepared by treatment under essentially anhydrous (dry) conditions, with an organic lithium in hexane, in an inert medium, e.g. a cyclic ether, such as tetrahydrofuran (THF), at reduced temperatures e.g. from about −45° C. under anhydrous conditions. To the resulting salt, in situ, is then added a silyl reagent of the formula IX:

wherein $R^1$, $R^2$ and $R^3$ are as defined above, and $Z^1$ is chloro or bromo preferably chloro, at reduced temperatures e.g. from about −20° to −10° C., e.g. about −15° C., also under essentially anhydrous conditions; the reaction medium for the first step also serving for the second step. The reaction mixture is then quenched with water and resulting compound VIII recovered.

In the process (d) the oxazoline of Formula VIII is N-methylated to obtain an oxazolinium compound, the preferred N-methylating agent being methyl iodide which yields an oxazolinium iodide of Formula VII. While as little as one mole of methyl iodide per mole of the oxazoline of Formula VIII may be employed, usually a large excess of methyl iodide is preferably employed. The reaction temperature is conveniently from about 20° C. to reflux, preferably not in excess of 100° C., more preferably about 40°-50° C. The reaction is run in an inert organic medium e.g. a cyclic ether such as tetrahydrofuran under essentially anhydrous conditions.

In process (e) the oxazolinium compound (VII) is reduced, by treating with at least an equivalent amount of sodium borohydride or lithium borohydride per mole of the oxazolinium iodide (preferably a slight excess is used) in an anhydrous lower alkanol preferably absolute ethanol or a mixture thereof with an ether such as tetrahydrofuran. The reaction temperature is conveniently from about −40° to +5° C., and preferably about 0° when sodium borohydride is used; and from about −40° to −20° C. when lithium borohydride is used.

In process (f) the product of process (e) is hydrolyzed to its corresponding aldehyde (VI) with a dilute aqueous acid, e.g., 2N. hydrochloric acid at 20°-100° C., preferably at about 50°-70° C. While as little as one equivalent of acid per mole of compound VII may be used, a large excess is usually utilized, e.g., 9-40 equivalents.

In process (f) the oxazolyl ring of a compound VI is converted to an aldehydic unit to obtain the corresponding compound V. The conversion is accomplished by heating a compound VI in the presence of an aqueous acid, e.g. dilute hydrochloric acid, e.g. at from about 30° to 70° C., preferably at about 60° C., preferably in the presence of a cosolvent e.g. an inert water-soluble solvent, e.g. a cyclic ether, such as tetrahydrofuran (THF).

In process (g) a compound V is converted to its corresponding compound IV. First the reagent Y is prepared by treating an olefinic reactant Y, e.g. cis-1-ethoxy-2-tri-n-butylstannyl ethylene, with n-butyl lithium in hexane, at about −78° C. under essentially anhydrous conditions, and then reacting the resultant reagent in situ with a solution of aldehyde (V) in dry THF, at about −78° C., under essentially anhydrous conditions. The resulting compound IV may be recovered or may be employed in subsequent process (h) without separation.

The olefinic reactant Y has the formula:

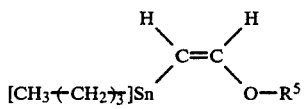

wherein $R^5$ is an n-alkyl as defined above. In a preferred reactant Y, $R^5$ is ethyl. Such materials are generally known and obtainable by methods known to the art, some being commercially available.

In process (h) the olefinic ether product of process (g) is treated under aqueous acidic conditions, preferably in an inert water-soluble medium, e.g. THF, at moderate temperatures, e.g. from about 15° to 80° C., preferably at from about 20° to 30° C. Acidic conditions are preferably provided by a catalytic amount of p-toluene sulfonic acid.

Process (i) consists of two steps. First reagent W, i.e. a lithium salt of an acetoacetic (lower)alkyl ester, preferaby the ethyl ester, is prepared by reacting at least two equivalents of a strong lithium base, e.g. butyl lithium or lithium diisopropylamide, with a $C_{1-4}$ alkyl ester of acetoacetic acid (W') in an inert medium, e.g. THF, at reduced temperatures, e.g. at about 0° C., under essentially anhydrous conditions. The salt thus obtained, may conveniently be reacted in situ with an aldehyde of formula III, at reduced temperatures e.g. at about −20° C., in an inert medium, e.g. THF, dry conditions being maintained. The strong lithium base reagent is conveniently employed as butyl lithium in an inert hydrocarbon medium, e.g. hexane, in the presence of diisopropylamine. After the reaction, any unreacted lithium compounds are decomposed by quenching with water, e.g. saturated aqueous ammonium chloride.

In process (j) compounds II (olefinic-hydroxyketones) are reduced to their corresponding olefinic diols (I'). The reduction is conveniently carried out by treating a compound II with triethylborane in an inert organic medium, e.g. a cyclic ether such as THF, at moderate temperatures, e.g. from about 20° to 35° C., under essentially anhydrous conditions; then reducing the temperature of the reaction mixture, e.g. to from about −75° to −90°, e.g. −80° to −85° C. and adding thereto sodium borohyride. At the end of the reaction an aqueous salt solution, e.g. saturated aq. ammonium chloride, is added to decompose any unreacted reagents. The resulting diol (I') is recovered, which is a final product of the invention. If desired, compounds I' may be saponified, neutralized or cyclized to yield further forms of compound I.

In process (k) compounds I' are saponified to obtain corresponding compounds $I^s$. This is achieved by treatment with aqueous alkali metal base, e.g. sodium hydroxide preferably in a water-miscible co-solvent, e.g. ethanol or dioxane, at moderate temperatures, e.g. from about 0° to 100° C., e.g. at about 75° C. Where a product is desired in which $R^4$ is hydrogen, i.e., the free acid form, such is obtained by acidifying the salt form (where $R^4 = M$) by conventional means, e.g. by addition of dilute hydrochloric acid.

Process (1) is accomplished by heating a compound I″ (in which $R_4 = H$) in an inert medium, e.g. an aromatic hydrocarbon such as toluene at from about 80° to 140° C., for example at the reflux temperature of the reaction medium.

Alternatively, a compound I' may be directly converted to its corresponding compound I″ by carrying out the procedure of process (k) and heating e.g. at about 80° to 140° C., e.g. at the refluxing temperature of the reaction medium, e.g. process (m).

Conversely, treating a compound I''' by saponifying and neutralizing will yield the corresponding compound I″.

Compounds I may also be viewed as consisting of two classes of compounds, i.e. compounds Ia where A=C, and Ib where A=D:

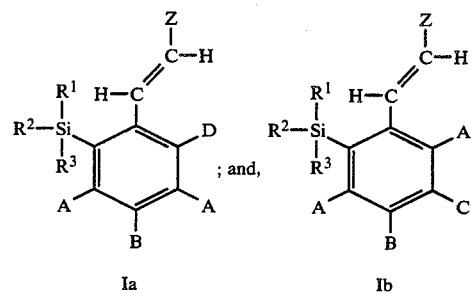

Ia                Ib in which Z, $R^1$, $R^2$, $R^3$, A, B, C and D, are as defined above.

Compounds Ia are conveniently prepared by method (a) described above, involving an oxazoline intermediate; however compounds Ib are preferably prepared by method (b) described hereinafter, involving a diels-Alder reaction, as method (a) tends to yield a mixture of products which are difficult to separate when employed for preparing products of type Ib. In addition, where difficulties are encountered in the preparation of any particular compound Ia, the use of method (b) may prove advantageous.

The preparation of compounds IIIb via method (b) is conveniently represented in Reaction Schemes C and D, below, wherein A, B, C, D, and E are as defined above, and $R^{5'}$ and $R^{5''}$ are, independently, alkyl having from 1 to 3 carbon atoms, preferably ethyl, and $Z^1$ is chloro or bromo.

The preparation of compounds I from compounds IIIb is conveniently accomplished in the same manner as that described with respect to Reaction Scheme B, above, for preparing compounds I from corresponding compounds III.

REACTION SCHEME C

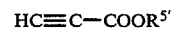 XV

-continued
REACTION SCHEME C

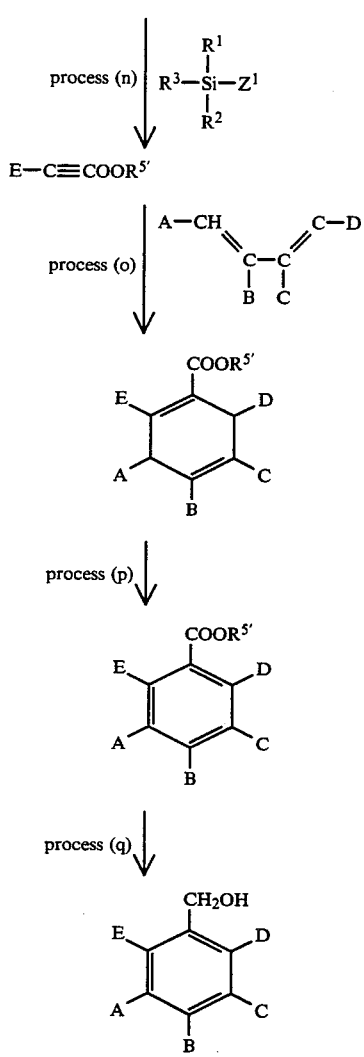

REACTION SCHEME D

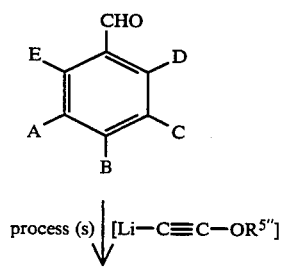

-continued
REACTION SCHEME D

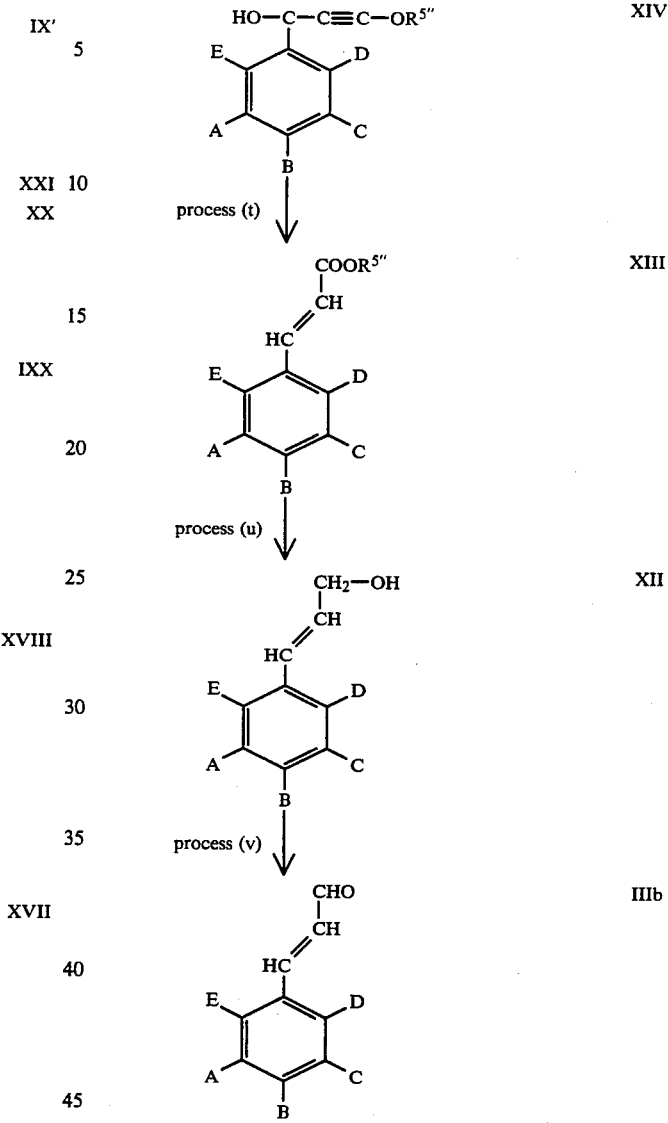

Process (n) provides reagent of formula XXI. The process involves two steps. In the first step the lithium salt of an alkyl ester of propiolic acid is prepared by reacting a propiolic ester (XV) with a strong lithium base, e.g. lithium diisopropylamide, at reduced temperatures e.g. at from about −80° to −65° C., e.g. at about −70° C., in an inert medium, e.g. a cyclic ether such as THF, under essentially anhydrous conditions. The second step involves reating, in situ, the resulting lithium-ester reagent with a $R^1$, $R^2$, $R^3$, bearing silyl halide (IX′) under similar conditions. Unreacted reagents are decomposed by adding an aqueous salt solution, e.g. saturated aqueous ammonium chloride to the reaction mixture, and the silyl-ester product (XXI) recovered.

Process (o) is a Diels-Alder reaction. The reagent of formula XII is reacted with a diene of formula XX, preferably at from about 180°-220° C., especially from about 190°-210° C., for under pressure, e.g. a closed system, for example, 2-5 days. A catalytic amount (e.g. 0.5-3 g per mole of the diene) of hydroquinone (to minimize polymerization of the diene) may be included, if desired. If necessary, a pressure vessel is utilized. The reaction may be run neat when at least one of the reactants is a liquid under the reaction conditions; in such a situation, an excess of such reactant(s) serves as the solvent. An inert organic solvent may, however, be utilized (and must be utilized when neither reactant is a liquid under the reaction conditions). Suitable solvents include the hydrocarbons, e.g. mono-, di- and trialkylbenzenes having a boiling point of at least 125° C., e.g. the xylenes. When a solvent is utilized, the molar ratio of the reactants may be 1:1. However, an excess of one reactant, usually the cheaper one, e.g., 1.1-5 moles of one reactant per mole of the other, is usually utilized.

In process (p) the cyclohexadiene product of the Diels-Alder reaction (process o) is aromatized by heating in an inert medium, e.g. an aromatic solvent, such as toluene or xylene, e.g. at the reflux temperature of the mixture with an aromatizing reagent, e.g. palladium on charcoal.

In process (q) the ester function of the aromatic compounds (XVIII) is reduced to obtain the corresponding alcohol of formula XVII. The reaction may be accomplished in a conventional manner. It is preferably carried out at reduced temperatures, e.g. from about $-80°$ to $-60°$ C., especially at $-78°$ C., in an inert organic medium, e.g. a hydrocarbon such as toluene, under essentially anhydrous conditions employing a vigorous organo-metallic hydride, e.g. diisolbutylaluminumhydride (DIBAL).

In process (r) the hydroxy function of the alcohol (XVII) is oxidized to obtain the corresponding aldehyde of formula XVI. The reaction may be accomplished in the conventional manner, e.g. at moderate temperatures, e.g. at from about 0° to 50° C., e.g. at 20°-30° C., in an inert medium, e.g. an organic solvent, such as a chlorinated lower alkane, e.g. methylene chloride, employing an oxidizing reagent, e.g. pyridinium dichromate.

In process (s) the aldehyde of formula XVI is reacted with a lithium salt reagent of formula XV' to obtain the corresponding acetylenically unsaturated ester compound of formula XIV. Reagents XV' are obtainable by treating an acetylenic ether of the formula XV:

     XV in which $R^{5''}$ is alkyl having from 1 to 3 carbon atoms, with a strong lithium base, e.g. an organo-lithium salt, such as butyl lithium, at reduced temperatures, e.g. from about $-80°$ C. to $-60°$ C., preferably at $-78°$ C., neat or in an inert organic medium, e.g. a cyclic ether, such as THF, under essentially anhydrous conditions, and employed without recovery. When the reaction is completed an aqueous solution, e.g. saturated aqueous sodium bicarbonate or sodium sulfate, is added to decompose any unreacted reagent.

In process (t) an acetylenically unsaturated alcohol of formula XIV is converted to a corresponding ethylenically unsaturated ester compound of formula XIII. The conversion is accomplished by treating the product of process (s) with a strong acid, e.g. p-toluenesulfonic acid in the presence of water and a water-miscible organic co-solvent, e.g. THF, at moderate temperatures, e.g. at from about 15° to 80° C., conveniently at from about 20° to 30° C., Processes (u) and (v) involve reduction of the ester function of a compound XIV to a hydroxy group, followed by the oxidation thereof to obtain the corresponding olefinic aldehyde (a compound III'). These reactions may be carried out in the conventional manner. It is particularly convenient to carry them out analogous to the procedures described above for processes (q) and (r), respectively.

Compounds IIIb may be converted to their corresponding compounds I, by following procedures analogous to those described above for converting compounds III to compounds I as outlined in Reaction Scheme B, above.

Reagents and starting materials described herein, e.g. compounds W, Y, IX'', XV, XV' and XX are known and obtainable by known means, or where not known, may be obtained by adaptation of methods reported in the literature for the preparation of known analogs; some compounds being commercially available.

The final products and intermediate compounds described herein may be recovered and refined, where such is desired, by conventional means, such as by crystallization, distillation or chromatographic techniques such as column or thin layer chromatography, e.g. silica gel column chromatography.

Evaporations are done under vacuum employing minimal heating. Drying of organic phases is done over anhydrous sodium sulfate, unless indicated otherwise.

UTILITY STATEMENT

The compounds of Formula I are competitive inhibitors of 3-hydroxy-3-methylglutaryl coenzyme A (HMG-CoA) reductase, the rate limiting enzyme in cholesterol biosynthesis, and, therefore, they are inhibitors of cholesterol biosynthesis. Consequently, they are useful for lowering the blood cholesterol level in animals, e.g., mammals, especially larger primates, and, therefore, as hypolipoproteinemic and anti-atherosclerotic agents. The biological activity of the compounds of Formula I is demonstrated in the following three tests:

Test A. In Vitro Microsomal Assay of HMG-CoA Reductase Inhibition

200 μl. aliquots (1.08-1.50 mg./ml.) of rat liver microsomal suspensions, freshly prepared from male Sprague-Dawley rats (150-225 g. body weight), in Buffer A with 10 mmol. dithiothreitol are incubated with 10 μl. test substance dissolved in dimethylacetamide and assayed for HMG-CoA reductase activity as described by Ackerman et al., J. Lipid Res. 18,408-413 (1977). In the assay the microsomes are the source of the HMG-CoA reductase enzyme which catalyzes the reduction of HMG-CoA to mevalonate. The assay employs a chloroform extraction to separate the product, [$^{14}$C]mevalonolactone, formed by the HMG-CoA reductase reaction from the subsubstrate, [$^{14}$C]HMG-CoA. [$^{3}$H]mevalonolactone is added as an internal reference. Inhibition of HMG-CoA reductase is calculated from the decrease in specific activity [$^{14}$C/$^{3}$H]mevalonate) of test groups compared to controls.

Test B. In Vitro Cell Culture Cholesterol Biosynthesis Screen

The cell culture is prepared as follows: Stock monolayer cultures of the Fu5AH rat hepatoma cell line (originally obtained from G. Rothblat; see Rothblat, Lipids 9, 526-535 (1974) are routinely maintained in Eagle's Minimum Essential Medium (EMEM) supplemented with 10% fetal bovine serum (FBS) in 75 cm². tissue culture flasks. For these studies, when the cultures reach confluence, they are removed by mild enzymatic treatment with 0.25% trypsin in Hanks' balanced salt solution (without calcium and magnesium). After centrifugation of the cell suspension and aspiration of the enzymatic solution, the cell pellet is resuspended in an appropriate volume of media for seeding into 60 mm. tissue culture dishes. The cultures are incubated at 37° C. in an atmosphere of high humidity and 5% carbon dioxide. When the cultures are confluent (approximately 5 days), they are ready for use. The culture media is aspirated from the dishes and replaced with 3 ml. of EMEM supplemented with 5 mg./ml. of delipidized serum protein (DLSP) prepared by the method of Rothblat et al., In Vitro 12, 554–557 (1976). Replacement of the FBS with DLSP has been shown to stimulate the incorporation of [$^{14}$C]acetate into sterol by removing the exogenous sterol supplied by the FBS, thereby requiring the cells to synthesize sterol. Enhanced 3-hydroxy-3-methylglutaryl Coenzyme A reductase (HMG-CoA reductase) activity is measurable in the cells in response to the lack of exogenous sterol. Following approximately 24 hours incubation at 37° C. in the DLSP supplemented media, the assay is initiated by the addition of 3μCi of [$^{14}$C]acetate and the test substances solubilized in dimethylsulfoxide (DMSO) or distilled water. Solvent controls and compactin-treated controls are always prepared. Triplicate 60 mm. tissue culture dishes are run for each group. After 3 hours incubation at 37° C., the cultures are examined microscopically using an inverted phase contrast microscope. Notations are made of any morphological changes which may have occurred in the cultures. The media is aspirated and the cell layer is gently washed twice with 0.9% sodium chloride solution (saline). The cell layer is then harvested in 3 ml. of 0.9% saline by gentle scraping with a rubber policeman and transferred to a clean glass tube with Teflon lined cap. The dishes are rinsed with 3 ml. of 0.9% saline and rescraped, and the cells are combined with the first harvest. The tubes are centrifuged at 1500 r.p.m. for 10 minutes in an IEC PR-J centrifuge, and the supernatant is aspirated.

The cells are then extracted as follows: One ml. of 100% ethanol is added to the cell pellet followed by sonication for 10 seconds with a "LO" setting of 50 on a Bronwell Biosonik IV. One hundred μL. are taken for protein determination. One ml. of 15% potassium hydroxide (KOH) is added, and the samples are thoroughly vortexed. Saponification is accomplished by heating the ethanol-KOH treated samples at 60° C. for 60 minutes in a water bath. Following dilution of the samples with 2 ml. of distilled water, they are extracted three times with 7 ml. of petroleum ether. The petroleum ether extracts are then washed three times with 2 ml. of distilled water and finally taken to dryness under a stream of nitrogen.

The obtained samples are then analyzed by thin layer chromatography (TLC) as follows: Residues from the petroleum ether extraction are taken up in a small volume of hexane and spotted on silica gel 60 TLC plates (E. Merck). Development of the plates is carried out in a 150 parts by volume hexane: 50 parts by volume diethyl ether: 5 parts by volume glacial acetic acid solvent system using a three phase development procedure. Visualization is accomplished in an iodine vapor chamber. The plates are divided into five sections such that each section contains the molecules having the following approximate Rf values: section 1-0-0.4, section 2-0.4-0.55, section 3-0.55-0.7, section 4-0.7-0.9 and section 5-0.9-1.0. Section 2 contains the non-saponifiable sterols. The five sections of the TLC plates are scraped into scintillation vials. Blanks are also prepared from scrapings of chromatographed non-labelled standards. ACS ® scintillation cocktail is added, and the radioactivity is determined in a liquid scintillation spectrometer. [$^{14}$C]hexadecane standards are used to determine counting efficiencies. The total protein content of the samples is determined employing the Bio-Rad Protein Assay System.

The results are reported as disintegrations per minute per mg. protein (d.p.m./mg. protein) for each of the five TLC sections. Mean d.p.m./mg. protein±standard error of the mean are calculated, and drug treated means are compared for percentage change (%Δ) and statistical significance with solvent control means. TLC section 2 data is taken as a measure of HMG-CoA reductase activity inhibition.

Test C: In Vivo Cholesterol Biosynthesis Inhibition Tests: In vivo studies utilize male Wistar Royal Hart rats weighing 150±20 g. which have been kept for 7–10 days on an altered light cycle (6:30 A.M.–6:30 P.M. dark) housed two per cage and fed powdered Purina Rat Chow and water ad libitum. Three hours before the diurnal maximum of cholesterol synthesis at mid-dark, the rats are administered the test substances dissolved or as a suspension in 0.5% carboxymethylcellulose in a volume of 1 ml./100 g. body weight. Controls receive vehicle alone. One hour after receiving the test substance, the rats are injected intraperitoneally with about 25 μCi/100 g. body weight of sodium [1-$^{14}$C]acetate 1-3 mCi/mmol. Two hours after mid-dark, blood samples are obtained under sodium hexobarbitol anesthesia and the serum separated by centrifugation.

Serum samples are saponified and neutralized, and the 3β-hydroxy sterols are precipitated with digitonin basically as described by Sperry et al., J. Biol. Chem. 187,97 (1950). The [$^{14}$C]digitonides are then counted by liquid scintillation spectrometry. After correcting for efficiencies, the results are calculated in nCi (nanocuries) of sterol formed per 100 ml. of serum. Inhibition of sterol synthesis is calculated from the reduction in the nCi of sterols formed from test groups compared to controls.

The following results were obtained on products of the Examples, hereinafter presented, employing test A, (microsomal assay) above; where the product was saponified M=Na, unsaponified products were tested in DMA:

| Product of Example | IC$_{50}$ (μM) | Form |
|---|---|---|
| 5a | 14.7 | Ia' |
| 5b | 17.1 | Ia$^s$ |
| 6a | 6.9 | Ia$^s$ |
| 6b | 16.4 | Ia''' |
| 6b | 14.2 | Ia$^s$ |
| 6g | 27.2 | Ia''' |
| 6g | 4.3 | Ia$^s$ |
| 8b | 52.4 | Ia$^s$ |
| 9 | 28.1 | Ib' |
| 10 | 24.4 | Ib''' |
| 10 | 9.0 | Ib$^s$ |
| compactin | 0.8 | (standard.) |

IC$_{50}$ is the concentration of the test substance in the assay system calculated to produce a 50% inhibition of HMG—CoA reductase activity.

The following results were obtained on products of the examples herein presented employing test B, above (cell culture):

| Product of Example | Concentration (μM) | % Inhibition | Form |
|---|---|---|---|
| 3 | 10. | 74 | Ia''' |
| 4 | 10. | 56 | Ia''' |
| 5a | 1. | 47 | Ia' |
| 5e | 10. | 28 | Ia' |
| 6a | 10. | 73 | Ia''' |
| 6g | 10. | 65 | Ia''' |
| 7a | 10. | 17 | Ia' |
| 8a | 10. | 33 | Ia''' |
| 9 | 1. | 19 | Ib' |
| 10 | 10. | 63 | Ib''' |
| compactin | 0.08 | 50 | (standard) |

The following results were obtained on products of the examples herein presented employing test C, above (in vivo inhibition):

| Product of Example | Dose mg/kg | % Inhibition | Form |
|---|---|---|---|
| 4 | 100 | 61 | Ia''' |
| 6g | 48 | 57 | Ia''' |
| compactin | 3.5 | $ED_{50}$ | standard |
| Mevinolin | 0.41 | $ED_{50}$ | standard |

As set forth above, the compounds of Formula I (including each and every subgroup thereof set forth in the specification and/or the claims) inhibit cholesterol biosynthesis and are useful for lowering the blood cholesterol level in animals, particularly mammals and more particularly larger primates, and, therefore, as hypolipoproteinemic and anti-atherosclerotic agents.

The compounds of Formula I may be formulated into conventional pharmaceutical compositions and administered by conventional modes of administration. The compounds of each and every subgroup thereof in the specification and/or claims may likewise be formulated into conventional pharmaceutical compositions.

The compounds of Formula I may be combined with one or more pharmaceutically acceptable carriers and, optionally, one or more other conventional pharmaceutical adjuvants and administered orally in the form of tablets, dispersible powders, granules, capsules, elixirs, suspensions and the like or parenterally in the form of sterile injectable solutions or suspensions. The compositions may be prepared by conventional means. The preferred pharmaceutical compositions from the standpoint of ease of preparation and administration are solid compositions, particularly tablets and capsules.

The precise dosage of the compounds of Formula I to be employed for inhibiting cholesterol biosynthesis depends upon several factors including the host, the nature and the severity of the condition being treated, the mode of administration and the particular compound employed. However, in general, satisfactory inhibition or reduction of cholesterol biosynthesis (i.e., satisfactory reduction of the blood cholesterol level and satisfactory treatment of hyperlipoproteinemia and atherosclerosis) is achieved when a compound of Formula I is administered orally at a daily dosage of 4–200, e.g., 10–100, mg./kg. body weight or, for most larger primates, a daily dosage of 300–8000, mg., suitably 300 to 3000, mg. for the more active compounds. For the compound of Example 6(g)*, the oral daily dosage is indicated to be 4–100, mg./kg. body weight or, for most larger primates, it is indicated to be about 300 to 2000 mg.

*in saponified form; Z=Z', M=Na

The daily dosage is usually divided into two to four equal portions or administered in sustained release form. A typical oral dosage of the compound of Example 6(g)* is indicated to be 200 mg. three times a day. Usually, a small dosage is administered initially, and the dosage is gradually increased until the optimal dosage for the host under treatment is determined. For administration by injection, a dosage somewhat lower than would be used for oral administration of the same compound to the same host having the same condition is usually employed. However, the above dosages are also typically used for i.v. administration.

*in saponified form; Z=Z', M=Na

A typical dosage unit for oral administration may contain 75–2500 mg. of a compound of Formula I. Preferred dosage units contain 75–1000 mg., especially 75–250 mg., of a compound of Formula I such as the compound of Example 6(g)*.

The compounds of Formula I (including those of each and every subgroup thereof) may be formulated into such pharmaceutical compositions containing an amount of the active substance that is effective for inhibiting cholesterol biosynthesis, such compositions in unit dosage form and such compositions comprising a solid pharmaceutically acceptable carrier.

A representative formulation prepared by conventional techniques for encapsulation in a hard gelatin capsule is:

| | |
|---|---|
| Compound of Formula I, e.g., the compound of Example 6g)* | 100 mg. |
| Corn starch | 149 mg. |
| Magnesium stearate | 1 mg. |

A representative formulation suitable for preparing tablets by conventional means is:

| | |
|---|---|
| Compound of Formula I, e.g., the compound of Example 6g)* | 50 mg. |
| Polyvinylpyrrolidone USP | 5 mg. |
| Powdered lactose | 134 mg. |
| Corn starch | 10 mg. |
| Magnesium stearate | 1 mg. |

With particular respect to the silyl radical provided by reagent IX', it is preferred that no more than two of $R^1$, $R^2$ and $R^3$ is aryl; more preferably two of $R^1$, $R^2$ and $R^3$ are alkyl, e.g. methyl, and it is especially preferred that $R^1=R^2$, It is preferred that when a radical R° is present, that the resulting ring be unsubstituted, i.e. that Q=H.

It is preferred that where two bulky groups, such as bromo groups or a branched alkyl or alkoxy are present on the same ring structure, that they are not in ortho-relationship to each other.

With particular respect to compounds Ia, preferably A=C, and that A is H or alkyl.

With particular respect to compounds Ib, preferably A=D=alkyl having from 1 to 3 carbon atoms; B=C=H or alkyl having from 1 to 3 carbon atoms;

It is also preferred that in preparing compounds Ib that in a reagent A=D and B=C, and that where R° is present, it is formed by B+C.

The following examples are illustrative of the invention. All temperatures are centigrade and room temperature is 20° to 30° C., unless indicated otherwise.

Where NMR characterization data is presented, the analysis is run in CDCl₃ and values given in ppm; digits in parenthesis are number of protons; and s=singlet, d=doublet, t=triplet, q=quartet, m=multiple and b is broad, and J is coupling factor, unless indicated otherwise.

EXAMPLE 1

Ethyl 7-[2-(methyldiphenylsily)-phenyl]-3,5-dihydroxy-6-heptenoate, erythro, trans; (a compound Ia').

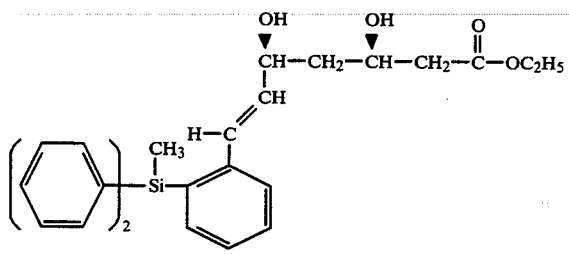

Step (a) N-(2-methyl-3-hydroxypropyl)-benzamide (a compound X)

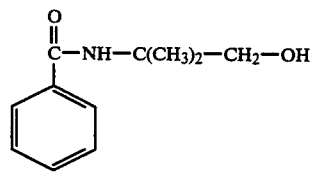

29 ml (0.25 mol) of benzoyl chloride in 100 ml of methylene chloride are added showly to a solution of 2-amino-2-methylpropanol in 100 ml of methylene chloride at 0°: The mixture is stirred for 4 hours at 0°, then filtered. The separated solids are washed with water. The filtrate is extracted three times with 50 ml portions of water. The combined aqueons extracts are acidified (with dilute hydrochloric acid) and extracted with ether. The combined organic extracts are dried, and then concentrated to give the product of this step as a white solid; NMR (CDCl₃): 1.4 (6H, s), δ3.65 (2H, s), 6.25–6.4 (1H, m), 7.4–7.85 (5H, m).

step (b) 6,6-dimethyl-2-phenyl-2-oxazoline (a compound IX)

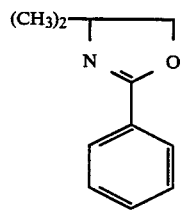

58.4 ml of thionyl chloride is added dropwise to 47 g of the amido product of Step (a) above, with stirring, and stirring maintained for 3 hours. The reaction mixture is then poured into 450 ml of ether and stirred for 5 minutes, then the mixture is filtered, and the recovered solids are washed with ether, and then transferred to a vessel, and 10% e.g. sodium hydroxide added, with stirring, to pH of about 9 to 10. The mixture is then extracted with ether and the combined extracts dried, and concentrated to give the crude product of this step as a clear oil, which upon distillation (b.p. 120° C. at 14 mm Hg) yields refined product of this step as a clear, colorless oil; NMR (CDCl₃): δ1.37 (6H, s), 4.1 (2H, s), 7.3–7.5 (3H, m), 7.8–8.0 (2H, m).

Step (c) 4,4-dimethyl-2-[2-(diphenylmethylsilyl)phenyl]4,5-dihydro-oxazole* ( a compound VIIII)

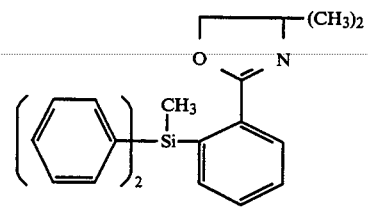

*also called [2-(6,6-dimethyl-oxazolyl)phenyl], diphenyl, methylsilane or 2-diphenylmethylsilyl-[2'-(6",6"-dimethyloxazolyl]-benzene.

20 ml of a 1.6 molar solution of butyl lithium (in hexane) is added to 5.1 g (2.914 mmol) of the oxazoline product of Step (b) in 25 ml of tetrahydrofuran at −45°. The reaction mixture is stirred for 2 hours, then 5.9 ml of diphenylmethylsilylchloride is added, and the resulting mixture stirred for 2 hours with slow warming to −15°, followed by quenching with water. The mixture is then extracted with methyltert.-butyl ether. The extract is then washed with water, and then saturated aqueous sodium chloride, dried and then concentrated to give crude product of this step as a yellow oil (12.8 g). The crude product is refined by chromatographing on a Waters prep. 500, using a silica gel column and a solvent system of 25% methyl tert.-butyl ether and 75% hexane (v/v) yielding the refined title product of this step obtained from the combined 5-7 fractions; NMR (CDCl₃): δ1.0(3H, s), 1.05(6H, s), 3.45(2H, s), 7.2–7.6(13H, m), 7.8–8(1H, m).

Step (d) 2-[2'-(diphenylmethylsilyl)phenyl]-4,5-dihydro-3,4,4-trimethyl-2-oxazolinium iodide (a compound VII)

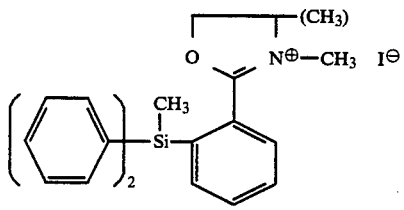

A mixture of 5.4 g (14.6 mmol) of the oxazoline product of Step (c), above, and 1.36 ml of methyl iodide in 15 ml of tetrahydrofuran (THF) are stirred at 40° for 2.5 days. The resulting precipitated solids are collected by filtration to give 2.75 g of pale yellow solids the filtrate is redissolved in 10 ml of THF and 1.4 ml of methyl iodide added, and the mixture stirred for 2 days at 45°, resulting in 1.55 g of a yellow precipitate, which is collected. The combined solids are used for the next step (1), below, without further purification; NMR (CDCl₃): δ0.9(3H, s), 1.35(6H, s), 3.43 (3H, s), 4.2(2H, s), 7.3–7.85(13H, m), 8.25–8.4(1H, m).

Step (e)
2-[2'(diphenylmethylsilyl)phenyl]-3,4,4-trimethyl-oxazolidine (a compound VI)

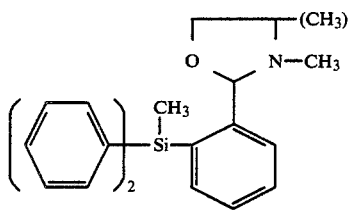

243 mg of sodium borohydride are added slowly to a suspension of 3.25 g of the iodide product of Step (d), above, in 10 ml of dry ethanol at 0°. The mixture is stirred for 4 hours the diluted with methyl tert.-butyl ether and washed with saturated aqueous sodium chloride (brine), dried and concentrated to give 2.35 g of the title product of this step as a clear oil. The product is used for the next step (f) without further purification, NMR (CDCl$_3$): $\delta$0.8(3H, s), 1.0(3H, s) 1.15(3H, s), 1.55(3H, s), 3.65(2H, q), 7.2–7.7(13H, m), 7.8–8 (1H, m).

Step (f) 2-diphenylmethylsilyl-benzaldehyde (a compound V)

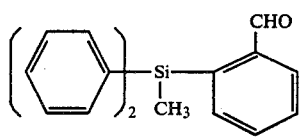

2.35 g of the product of Step (e), above, is heated in a mixture 12 ml of THF and 6 ml of 2N hydrochloric acid, at 60° for 5 hours. The reaction mixture is then diluted with methyl tert.-butyl ether and washed with 2N hydrochloric acid and then brine. The aqueous phases are combined and extracted thrice with methyl tert.-butyl ether. The combined organic extracts are washed with aqeons sodium carbonate, dried and concentrated to give 1.58 g of the title aldehyde product of this step, NMR(CDCl$_3$) $\delta$0.95 (3H, s), 7.2–7.7(13H, m), 7.85–8.05(1H, m), 10(1H, s).

Steps (g) and (h):
2-(diphenylmethylsilyl)-2-ethoxyethynyl-benzenemethanol, (a compd)-and 3-[2-(diphenylmethylsilyl)phenyl]-2-propanol (compounds IV and III)

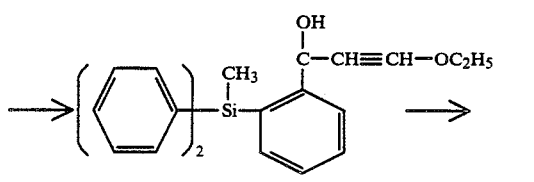

1.57 ml of 1.5 m solution of n-butyl lithium in hexane is added to a solution of 0.826 ml of cis-1-ethoxy-2-tri-n-butylstannyl ethylene in dry THF at −78°, under a nitrogen atmosphere. The resulting solution is stirred for 1.5 hours and then a solution of 0.58 g of the aldehyde product of Step (f) above, in 2 ml dry THF added thereto. The resulting mixture is stirred for 3 hours at −78°, then quenched by adding saturated aqueous ammonium chloride, and extracting with methyl tert.-butyl ether. The organic solution is dried, and concentrated to give the crude intermediate as a yellow oil. The intermediate is refined by dissolving in 15 ml of acetonitrile and washed thrice with 5 ml portions of pentane. The acetonitrile solution is then concentrated to give 650 mg. of refined intermediate (as a pale yellow oil).

The intermediate is dissolved in 10 ml of 90% aqueous THF, and treated with 500 mg of p-toluenesulfonic acid at room temperature for 3 hours. The mixture is diluted with methyl tert.-butyl ether, washed with aqueous sodium bicarbonate and brine, dried, and concentrated to give 500 mg of olefinic aldehyde product of this step as a white solid, NMR (CDCl$_3$) $\delta$0.9(3H, s), 6.45(1H, dd), 7–8 ppm(15H, m), 9.15(1H, d).

Step (i) ethyl
7-[2-methyldiphenylsilyl)-phenyl]-5-hydroxy-3-oxo-6-heptenoate, 6E, (a compound II)

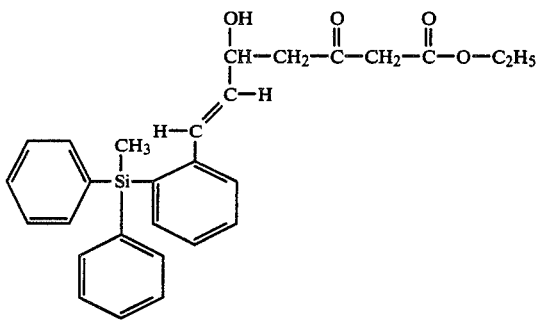

2.48 ml of a 1.6M solution of n-butyl lithium in hexane is added to 0.595 ml of diisopropylamine in 4 ml of dry THF at 0°. The mixture is stirred for 15 minutes, then 0.253 ml of ethyl acetoacetate is added. After stirring for 1.5 hours, the temperature is dropped to −20°, and 490 mg of the olefinic aldehyde product of Step g, above in 2 ml of dry THF is added. The reaction mixture is stirred for 3 hours at −20°, then quenched with sat. e.g. ammonium chloride. The resulting mixture is extracted with methyl tert. butyl ether. The organic phase is dried and concentrated to give crude product of this step as a yellow oil. The oil is chromatographed using 230–400 mesh silica gel packed to a depth of 6 inches in a 2½ inch diameter column with an eluting solvent of hexane/ethyl acetate (2:1 v.v); 30 ml fractions are taken of which the 18th to 24th are combined and concentrated to give 290 mg of refined olefinic ester product of this step, as a clear oil; NMR (CDCl$_3$) $\delta$0.1 (3H,s), 1.3 (3H,t), 2.5(2H,m), 3.4(2H,s) 4.2(2H,q), 5.9(1H,dd), 6.65 (1H,d), 7.2–7.6(14H,m).

Step (j) ethyl 7-[2-(methyldiphenylsilyl)-phenyl]-3,5-dihydroxy-6-heptenoate,(erythro, trans).

700 ml of a /molar solution of triethylborane in dry THF is added to a solution of the hydroxyketone product of Step i, above, in dry THF, at room temperature. After stirring for 2 hours, the temperature is dropped to −80°, and sodium borohydride added. The reaction mixture is stirred for 22 hours at from −80° to −85°, then saturated aqueous ammonium chloride added and the mixture extracted with methyl tert.-butyl ether. The organic extract is dried and concentrated to obtain crude product of this example as a residue. The residue is dissolved in 10 ml of methanol and 10 ml of pH 7 phosphate and treated with 5 ml of 30% hydrogen peroxide at room temperature. After stirring for 2 hours the mixture is partially concentrated by removing most of the methanol on a rotary evaporator. The resulting residue is extracted with methyl tert.-butyl ether. The resulting solution is washed with brine, e.g. sodium bisulfite, e.g. sodium bicarbonate and then brine, dried and concentrated to give 293 mg of refined product of this example as a pale yellow oil, NMR (CDCl$_3$) δ0.85(3H,s), 1.25 (3H,t), 2.35(2H,d), 4.15(2H,q), 3.9–4.3(2H,m), 5.85(1H, dd), 6.6(1H,d), 7.1–7.6(14H,m).

EXAMPLE 2

3,5-dihydroxy-7-[2-(methyldiphenylsilyl)-phenyl]-6-heptenoic acid (erythro, trans); (a compound Ia″)

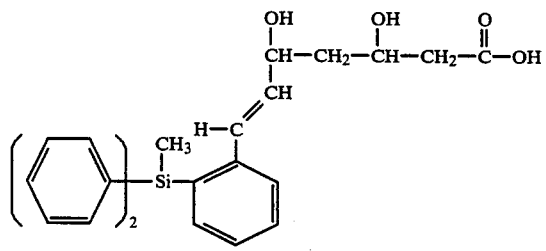

A solution of 290 mg of the dihydroxyester product of Example 1, above, in 1 ml of 1N aqueous sodium hydroxide and 4 ml of ethanol, is heated for 4 hours at 75°. The reaction mixture is then concentrated to obtain a residue (crude sodium salt of the product of this example) which is then suspended in water and acidified to pH3 with concentrated hydrochloric acid. The resulting mixture is extracted once with methylene chloride and twice with methyl tert.-butyl ether*. The combined organic extract is treated with charcoal, dried and concentrated to give 220 mg of the product of this example as an orange oil, which crystallizes on standing, NMR (CDCl$_3$) δ 0.9(3H,s), 2.5(2H,d), 4–4.3(2H,m), 5.8(1H,dd), 6.6(1H,d), 7.2–7.6(14H,m).
*MTBE

EXAMPLE 3

4-Hydroxy-6{2-[2-(methyldiphenylsilyl)phenyl]ethenyl}-2H-tetrahydropyran-2-one(trans,trans) (a compound Ia‴).

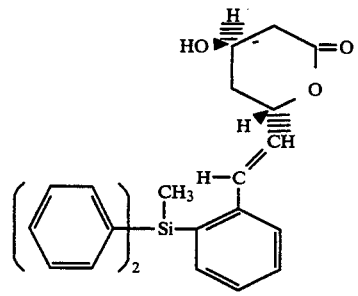

220 mg of the heptenoic acid product of Example 2, above, in 2 ml of toluene was heated to 110° for 1.5 hours, then cooled. A pale yellow solid crystallized. The solid is dissolved in methlene chloride and washed with aqueous sodium bicarbonate and water. The organic solution is treated with charcoal, dried and concentrated to give 157.7 mg of a pale yellow solid, which is recrystallized from toluene to give refined product of this example as an off-white solid, mp 173°–175°, NMR(CDCl$_3$) δ 0.95(3H,s) 1.5–1.7(3H,m), 2.55(2H,m), 4.15(1H,m), 5.0(1H,m), 5.95(1H,dd), 6.7(1H,d), 7.1–7.6(14H,m).

EXAMPLE 4

Following the procedure of Example 1, but using in place of the diphenylmethylsilylchloride (in Step c) used therein, an approximately equivalent amount of dimethylphenylsilylchloride, there is accordingly obtained ethyl 7-[-(dimethylphenylsilyl)-phenyl]3,5-dihydroxy-6-heptenoate, (erythro,trans), which upon saponification and neutralization according to the procedures of Examples 2 and 3, above, yields first the corresponding sodium salt ($R^4$=Na), the free acid thereof $R^4$=H), and then the corresponding lactone form, i.e. 4-Hydroxy-6{2-[2-(dimethylphenylsilyl)phenyl]ethenyl}-2H-tetrahydropyran-2-one (a compound Ia″); m.p. 92°–97°, NMR: 7.2–7.6(m,9H), 6.7(d,1H), 5.9(dd,H), 5.05(m,1H), 4.2(m,1H), 2.6(m,1H), 1.5–1.9(m,3H), 0.55(s,6H).

EXAMPLE 5

Following the procedure of Example 4, but using in place of the benzoyl chloride I.e. Step (a) used therein, an approximately equivalent amount of:
(a) 2.4-dimethylbenzoyl chloride;
(b) 4-chloro-2-methyl-benzoyl chloride;
(c) 2-methyl-4-phenyl-benzoyl chloride;
(d) 2-methyl-4-tert.-butyl-benzoyl chloride;
(e) 4-methoxy-2-methyl-benzoyl chloride;
(f) 2-chloro-4-methoxy-benzoyl chloride;
(g) 2-methylbenzoyl chloride,
there is according obtained compounds Ia′ of the structure:

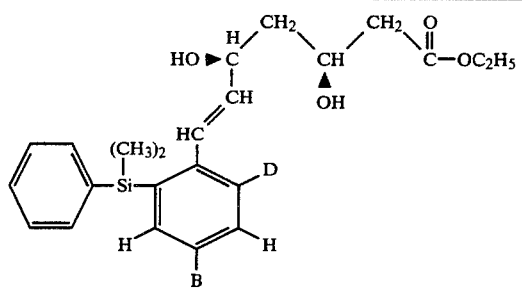

| | B | D | Notes: |
|---|---|---|---|
| (a) | Me | Me | |
| (b) | Cl | Me | |
| (c) | ph. | Me | |
| (d) | t-bu. | Me | |
| (e) | OMe | Me | |
| (f) | OMe | Cl | |
| (g) | H | Me | |

Code:
Me = methyl; t-bu. = tert.-butyl; ph. = phenyl; OMe = methoxy; and Cl = chloro

EXAMPLE 6

Treating the products of Examples 5a to 5g according to the procedures of Example 2, there is accordingly obtained the respective products, being first the sodium product Ia$^s$ by the saponification step:

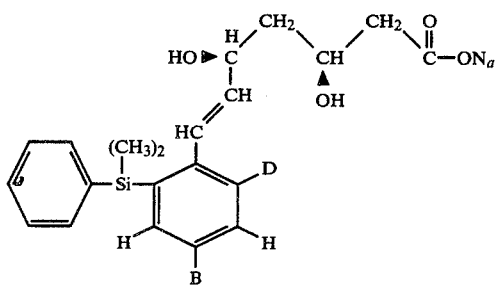

and then the corresponding free acids thereof (Ia″) upon nuetralization:

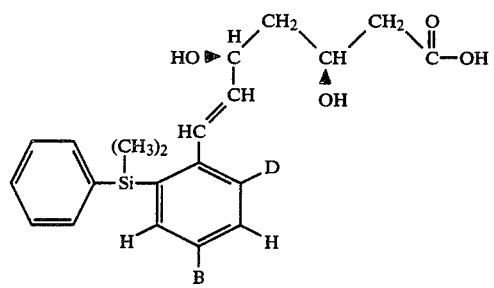

Treating the resultant free acids (Ia″) according to the procedure of Example 3, the corresponding lactone products (Ia‴) are respectively obtained:

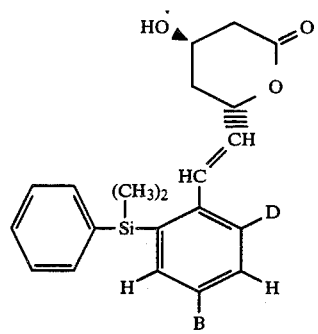

Ia‴

| | B | D |
|---|---|---|
| (a) | Me | Me |
| (b) | Cl | Me |
| (c) | ph. | Me |
| (d) | t-bu. | Me |
| (e) | OMe | Me |
| (f) | OMe | Cl |
| (g) | H | Me |

Code:
Me = methyl; t-bu. = tert.-butyl; ph. = phenyl; OMe = methoxy; and Cl = chloro

EXAMPLE 7

Following the procedure of Example 1, but using in place of benzoyl chloride used therein, in Step (a), an approximately equivalent amount of:

(a) 4-chloro-2-methyl-benzoyl chloride; or
(b) 2-methyl-benzoyl chloride; there is accordingly obtained the respective compounds Ia′, which upon saponification and neutralization according to the method of Example 2, yields first the corresponding sodium salts (Ia$^s$), then the corresponding free acids (Ia″):

| | B | D |
|---|---|---|
| (a) | Cl | CH$_3$ |
| (b) | H | CH$_3$ |

EXAMPLE 8

Treating the free acid products 7(a) and 7(b) obtained in Example 7, above, by the procedure of Example 3, there are accordingly obtained the corresponding lactones of the structure Ia‴:

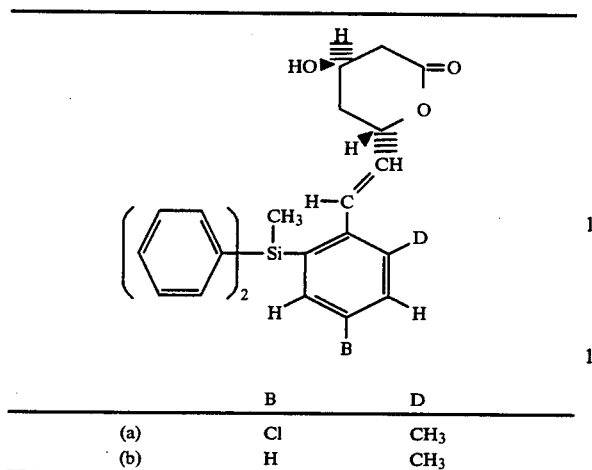

| | B | D |
|---|---|---|
| (a) | Cl | CH₃ |
| (b) | H | CH₃ |

EXAMPLE 9

Ethyl 7-[3,6-dimethyl-(2-dimethylphenylsilyl)-phenyl]-3,5-dihydroxy hept-6-enoate, (erythro,trans); (a compound Ib')

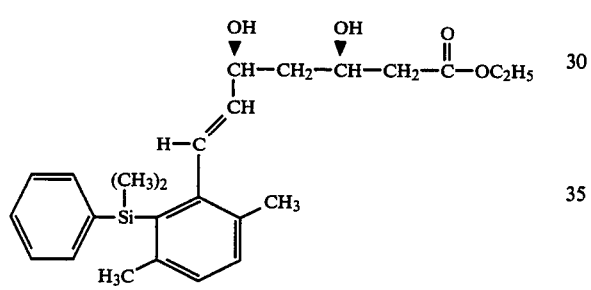

Step (n) ethyl 4-methyl, 4-phenyl-4-sila-pent-2-ynoate (a compound XXI).

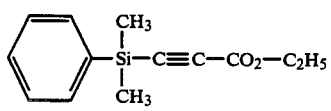

Ethyl propiolate (20 g, 204 mmol) was added dropwise to lithium diisopropyl amide THF at −70°. The mixture was stirred for 1.5 hours, then 44 ml (1.3 equivalents) of phenyldimethylchlorosilane in 50 ml of THF was added dropwise. The reaction was stirred 18 hours at −75°, then quenched with aqueous ammonium chloride and extracted with MTBE. The organic solution was treated with charcoal, dried, concentrated on a rotary evaporator, and distilled under reduced pressure (at about 0.5 mm Hg) using a kugelrohr apparatus to give 44.5 g of product which was chromatographed on silica gel using 10% diethyl ether in hexane as the eluent to yield the product of this step. The lithium diisopropyl amide was made from 30.6 ml of diisopropylamine 123 ml of 1.6M n-butyl lithium in hexane, and 200 ml of THF.

Step (o) ethyl 3,6-dimethyl 2-(dimethylphenylsilyl)cyclohexa-1,4-dien-oate, (a compound IXX)

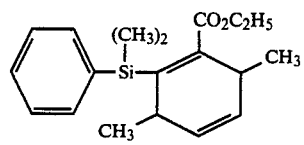

A mixture of 10 g (3.6 equivalents) of 2,4-hexadiene and 7.8 g (33.6 mmol) of the silylacetylenic ester product of step (n) above, was heated in a stainless steel bomb for 2.5 days at 180°–190°. The resulting mixture was concentrated on a rotary evaporator to give the crude product of this step (17.3 g). The material was distilled at reduced pressure (0.5 mm Hg) using a Kugelrohr apparatus to give about 9.85 g of refined product of this step.

Step (p) ethyl 3,6-dimethyl 2-(dimethylphenylsilyl)benzoate, (a compound XVIII)

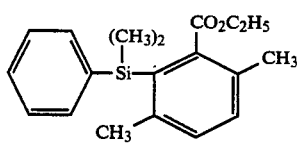

A mixture of the cyclohexadiene product of step (o) above (9.8 g, 31.2 mmol) and Pd/C (20 g) was heated to reflux in 250 ml of toluene for 24 hours. The mixture was then cooled, concentrated on a rotary evaporator, and distilled at reduced pressure (~0.5 mm Hg) using a kugelrohr apparatus to give product (8.55 g) as a pale yellow oil. The material was then chromatographed on silica gel using a Waters Prep 500 with 5% MTBE in hexane as the eluent; 4.3 g of refined benzoate product of this step was obtained and used in the next step.

Step (q) 3,6-dimethyl 2-(dimethylphenylsilyl)-benzyl alcohol (a compound XVII)

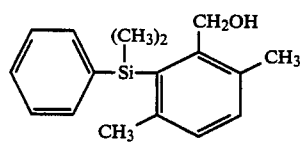

A 1M solution of diisobutylaluminumhydride in toluene (41 ml) was added to a solution of 4.26 g (13.65 mmol) of the benzoate product of step (p) above in 20 ml of toluene at −78°. The reaction was stirred 5 hours with gradual warming to −10°, then methanol (1.6 ml) was added followed by saturated aqueous ammonium chloride. The mixture was diluted with MTBE and filtered through a fritted glass filter. The solid was washed with MTBE and the filtrate was dried and concentrated on a rotary evaporator to give 3.85 g of product of this step as a clear oil.

Step (r)
3,6-dimethyl-2-(dimethylphenylsilyl)benzaldehyde (a compound XVI)

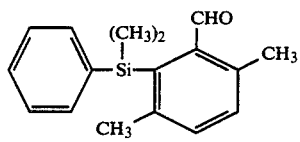

Pyridinium dichromate (9.24 g, 1.8 equivalents) was added to a methylene chloride solution of the benzyl alcohol product of step (q), above, at room temperature. The reaction was stirred for 24 hours, then diluted with diethyl ether and filtered. The filtrate was concentrated on a rotary evaporator and the residual oil was taken up in MTBE and washed with 2N hydrochloric acid, aqueous NaHCO₃, brine, treated with charcoal, dried and concentrated on a rotary evaporator to give the product of this step as a pale yellow oil. The product was distilled under reduced pressure (~0.5 mm Hg) using a Kugelrohr apparatus to give 3.3 g of refined product as a clear oil.

Step (s) ethyl 3-[3,6dimethyl-2-(dimethylphenylsilyl)phenyl]-3-hydroxy-prop-1-ynoate* (a compound XIV)

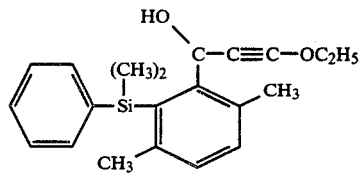

*Also known as 2-(dimethylphenylsilyl)-α-(2-ethoxyethynyl)-3,6-dimethyl benzenemethanol n-Butyl lithium was added to ethoxy acetylene at −78°. The reaction was stirred for 1 hour, then 2.63 g of the benzaldehyde then added to the product of step (r) above, in 10 ml of THF, was dropwise. The reaction was stirred for 5.5 hours at −78° then quenched with aqueous NaHCO₃, extracted with MTBE, dried and concentrated on a rotary evaporator to give 3 g of the product of this step as a pale yellow oil.

Step (t) ethyl 3-[2,5-dimethyl-6-(dimethylphenylsilyl)phenyl]-prop-2-enoate (a compound XIII)

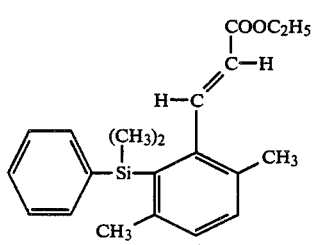

p-Toluenesulfonic acid (1.9 g) was added to a solution of 3 g of the product of step (s) above in 90% THF (aq.) at room temperature. The reaction was stirred for 2.5 hours, then diluted with MTBE, dried, and concentrated to give crude olefinic product of this step. The crude product was chromatographed on a 3"×6.5" silica gel (230–400 mesh) column using 10% diethyl ether in hexane as the eluent. The refined product of this step (1.16 g) had an m.p. of 81°-82°.

Step (u)
3-[2,5-dimethyl-6-(dimethylphenylsilyl)phenyl]prop-2-enol (a compound XII)*

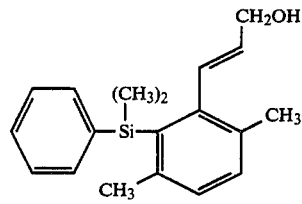

*Also called {2-[2-(dimethylphenylsilyl)3,5-dimethyl]phenyl}ethenylmethanol

A 1M solution of DIBAL in toluene (8.6 ml) was added slowly to the ester product of step (t) above (0.967 g, 2.86 mmol) in 5 ml of toluene at −78°. The reaction was stirred 4 hours with slow warming to 0°. The reaction was then re-cooled (−40°) and quenched with saturated aqueous sodium sulfate. Solid sodium sulfate and celite were added and the mixture was diluted with MTBE, stirred 10 minutes, and then filtered. The filtrate was concentrated to give 0.97 g of a clear oil which was chromatographed on silica gel (230–400 mesh) using a 3"×6.5" column with a 3:1 mixture of hexane and ethyl acetate as the eluent; 602 mg (71%) of refined alcohol product of this step was obtained.

Step (v)
3-[2,5-dimethyl-6-(dimethylphenylsilyl)phenyl]prop-2-enal (a compound IIIb)

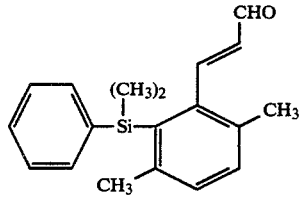

Pyridinium chlorochromate (772 mg, 1.8 equivalents) was added to a methylene chloride solution (5 ml) of the alcohol product of step (u), above, (582 mg) at room temperature. The reaction was stirred for 4 hours, then diluted with 15 ml of diethyl ether. Celite was added and the mixture was filtered through a pad of magnesium sulfate. The filtrate was concentrated and the residue was taken up in MTBE and washed with 2N HCl, brine, aqueous NaHCO₃, treated with charcoal, dried, and concentrated to give 536 mg of the aldehyde product of this step.

Following the procedure of steps (i) and (j) of Example 1, but using in place of the 3-[2-diphenylmethylsilyl)-phenyl]-2-propenal (a compound III) used therein, approximately an equivalent amount of the aldehyde product of step v above, there is accordingly obtained the product of this example, ethyl 7-[3,6-dimethyl-(2-dimethylphenylsilyl)-phenyl]-3,5-dihydroxy hept-6-enoate (erythro,trans).

EXAMPLE 10

Following the procedure of Examples 2 and 3, using the product of Example 9 as a compound I', there is accordingly (obtained the corresponding sodium salt, then the free acid thereof, and then the corresponding compound Ib''', which is 6-{2-[3,6-dimethyl-2-(dimethylphenylsilyl)phenyl]ethenyl}4-hydroxy-tetrahydro-2H-pyran-2-one (trans,trans).

| Example No. | CHARACTERIZATION NMR |
|---|---|
| 5a | 7.15–7.5(m,6H), 7.0(m,1H), 6.45(d,1H), 5.35(dd,1H), 4.2(m,4H), 2.3–2.5(m,2H), 2.35(s,3H), 2.25(s,3H), 1.25–1.7(m,7H), 0.55(s,6H) |
| 5b | 7.45(m,7H), 6.4(d,1H), 5.45(dd,1H), 4.2(m,4H), 2.5(m,2H), 2.2(s,3H), 1–1.6(m,7H), 0.55(s,6H) |
| 5c | 7.2–7.7(m,12H), 6.5(d,1H), 5.4(m,1H), 4.2(m,4H), 2.45(m,2H), 2.35(s,3H), 1.2–1.7(m,7H), 0.6(s,6H) |
| 5e | 7.2–7.6(m,5H), 7(m,1H), 6.75(m,1H), 6.4(d,1H), 5.4(m,1H), 4.2(m,4H), 3.8(s,3H), 2.45(m,2H), 2.25(s,3H), 1–1.7(m,7H), 0.65(s,6H) + some impurities |
| 5f | 7.15–7.5(m,5H), 6.9(m,2H), 6.35(d,1H), 5.55(m,1H), 4.15(m,4H), 3.75(s,3H), 2.45(m,2H), 1.1–1.7(m,7H), 0.55(s,6H). |
| 6a | 7.45(m,2H), 7.35(m,3H), 7.25(s,1H), 7.1(s,1H), 6.6(d,1H), 5.42(dd,H1), 5.05(m,1H), 4.25(m,1H), 2.65(m,2H), 2.35(s,3H), 2.25(s,3H), 1.5–1.8(m,3H), 0.55(s,3H) |
| 6b | 7.2–7.5(m,7H), 6.5(d,1H), 5.4(dd,1H), 5.05(m,1H), 4.25(m,1H), 2.65(m,2H), 2.2(s,3H), 1.2–1.7(m,3H), 0.55(s,3H) |
| 6c | 7.25–7.7(m,12H), 6.65(d,1H), 5.5(dd,1H), 5.1(m,1H), 4.25(m,1H), 2.2(m,2H), 2.35(s,3H), 1.5–1.9(m,3H), 0.6(s,6H) |
| 6f | 7.2–7.6(m,5H), 7.05(d,1H), 6.95(d,1H), 6.5(d,1H), 5.65(dd,1H), 5.1(m,1H), 4.25(m,1H), 3.8(s,3H), 2.65(m,2H), 1.4–1.9(m,3H), 0.55(s,6H) |
| 6g | 7.1–7.5(8H,overlapping multiplets), 6.6(d,1H), 5.45(dd,1H), 5.1(m,1H), 4.25(m,1H), 2.65(m;2H), 2.25(m,3H), 1.25–1.9(overlapping mult. 3H), 0.55(s,6H) |
| 7a | 7–7.7(m,12H), 6.4(m,1H), 5.3(m,1H), 4.2(m,4H), 2.4(m,2H), 2.25(s,3H), 1.1–1.7(m,7H), 0.75(s,3H) |
| 8a | 7.1–7.7(m,12H), 6.5(d,1H), 5.4(dd,1H), 4.95(m,1H), 4.15(m,1H), 2.6(m,2H), 2.25(s,3H), 1.1–1.7(m,3H), 0.85(s,3H) |
| 8b | 7.1–7.55(m,13H), 6.6(d,1H), 5.4(dd,1H), 4.95(m,1H), 4.15(m,1H), 2.6(m,2H), 2.3(s,3H), 1.2–1.7(m,3H), 0.7(s,3H) |
| 9 | 7.2–7.5(m,5H), 7.1(d,1H), 6.97(d,1H), 6.45(d,1H), 5.25(dd,1H), 4.2(m,4H), 2.25–2.5(m.2H), 2.35(s,3H), 2.15(s,3H), 1.4–1.7(m,4H), 1.25(t,3H), 0.55(s,6H) |
| 10 | 7.45(m,2H), 7.3(m,3H), 7.1(d,1H), 7.0(d,1H), 6.7(d.1H), 5.35(dd,1H), 5.1(m,1H), 4.3(m,1H), 2.7(m,1H), 2.3(s,3H), 2.17(s,3H), 1.65–1.95(m,3H), 0.6(s,6H). |

What is claimed is:
1. A compound of the formula:

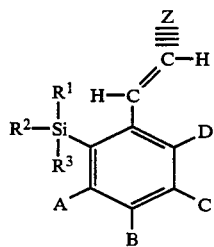

wherein each of $R^1$, $R^2$ and $R^3$ is independently, alkyl having from 1 to 4 carbon atoms; or phenyl which may be unsubstituted or substituted either by one or two alkyl or alkoxy groups having from 1 to 3 carbon atoms, or chloro; or by one fluoro, bromo or trifluoromethyl substituent;

A is a hydrogen atom or alkyl having from 1 to 3 carbon atoms,

B is a hydrogen atom; alkyl or alkoxy having from 1 to 4 carbon atoms; halo having an atomic weight of from about 19 to 80, trifluoromethyl; or phenyl, benzyl, or benzyloxy, wherein the aromatic portion may be unsubstituted, or substituted by up to two groups, one of which may be fluoro, bromo or trifluoromethyl; or one or two of which may be alkyl or alkoxy having from 1 to 4 carbon atoms, or chloro;

C is a hydrogen atom, alkyl or alkoxy having from 1 to 4 carbon atoms, halo having an atomic weight of from about 19 to 80, or trifluoromethyl; and D is a hydrogen atom, alkyl or alkoxy having from 1 to 4 carbon atoms, halo having an atomic weight of from about 19 to 80 or trifluoromethyl;

and any of A+B, B+C, or C+D may constitute a 4 carbon radical of the formula R°; which is either R°¹:

—CH=CH—CH=CH—; or R°²:
—(CH₂)₄—;

and that the ring formed by the radical R° may bear one halo having an atomic weight of from about 19 to 80, or alkyl or alkoxy substituent having from 1 to 4 carbon atoms; and Z is a radical of the formula Z';

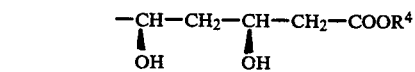

or a radical of the formula Z":

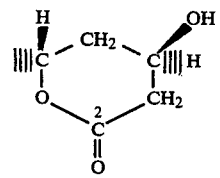

wherein $R^4$ is hydrogen, $C_{1-4}$alkyl, and benzyl; or M;
wherein M is a cation forming a pharmaceutically acceptable salt with the provisions that there be no more than one trifluoromethyl group and no more than two bromos present on the molecule.

2. A compound of claim 1 in which Z is of type Z'.
3. A compound of claim 1 in which Z is of type Z".
4. A compound of claim 2 in which $R^4$ is of type $R^{4'}$ which is either a hydrogen atom, or an equivalent of a cation which forms a pharmaceutically acceptable salt.
5. A compound of claim 2 wherein $R^4$ is alkyl.
6. A compound of claim 2 wherein each of $R^1$ and $R^2$ is unsubstituted phenyl and $R^3$ is methyl.
7. A compound of claim 2 in which each of $R^1$ and $R^2$ is methyl and $R^3$ is unsubstituted phenyl.
8. A compound of claim 6 in which A and C are the same.
9. A compound of claim 6 in which A and D are the same.
10. A compound of claim 3 wherein each of $R^1$ and $R^2$ is unsubstituted phenyl and $R^3$ is methyl.
11. A compound of claim 3 in which each of $R^1$ and $R^2$ is methyl and $R^3$ is unsubstituted phenyl.
12. A compound of claim 11 in which A and C are the same.

13. A compound of claim 11 in which A and D are the same.

14. A compound of claim 5 in which $R^4$ is a ethyl.

15. A compound of claim 4 in which $R^{4'}$ is a hydrogen atom.

16. A compound of claim 4 in which $R^{4'}$ is a sodium.

17. A compound of claim 7 in which $R^{4'}$ is sodium.

18. The compound of claim 13 in which D is methyl and each of A, B and C is a hydrogen atom.

19. A method of claim 21, comprising administering to said mammal from about 300 to about 8000 milligrams per day of said compound.

20. A composition useful for treating atherosclerosis in a mammal in need of such treatment, comprising an effective amount of a compound and an inert non-toxic, pharmaceutically acceptable carrier; the amount of compound, being an amount effective for inhibiting cholesterol biosynthesis in a mammal; said compound having the formula:

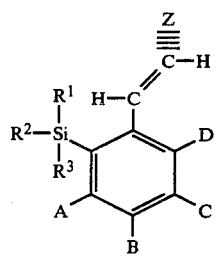

wherein each of $R^1$, $R^2$ and $R^3$ is independently, alkyl having from 1 to 4 carbon atoms; or phenyl which may be unsubstituted or substituted either by one or two alkyl or alkoxy groups having from 1 to 3 carbon atoms, or chloro; or by one fluoro, bromo or trifluoromethyl substituent;

A is a hydrogen atom or alkyl having from 1 to 3 carbon atoms, B is a hydrogen atom; alkyl or alkoxy having from 1 to 4 carbon atoms; halo having an atomic weight of from about 19 to 80, trifluoromethyl; or phenyl, benzyl, or benzyloxy, wherein the aromatic portion may be unsubstituted, or substituted by one or two groups, one of which may be fluoro, bromo or trifluoromethyl; or one or two of which may be alkyl or alkoxy having from 1 to 4 carbon atoms, or chloro;

C is a hydrogen atom, alkyl or alkoxy having from 1 to 4 carbon atoms, halo having an atomic weight of from about 19 to 80, or trifluoromethyl; and D is a hydrogen atom, alkyl or alkoxy having from 1 to 4 carbon atoms, halo having an atomic weight of from 19 to 80 or trifluoromethyl;

and any of A+B, B+C, or C+D may constitute a 4 carbon radical of the formula R°; which is either $R^{°1}$:

—CH=CH—CH=CH—; or $R^{°2}$:

—(CH$_2$)$_4$—; with the provisions that the ring formed by the radical R° may bear one halo having an atomic weight of from about 19 to 80, or alkyl or alkoxy substituent having from 1 to 4 carbon atoms; and Z is a radical of the formula Z':

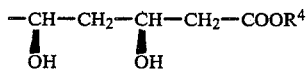

a radical of the formula Z'':

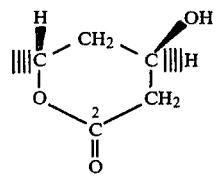

wherein $R^4$ is hydrogen, $C_{1-4}$alkyl, or benzyl; or M;

wherein M is a cation forming a pharmaceutically acceptable salt:

with the provisions that there be no more than one trifluoromethyl group and no more than two bromos present on the molecule.

21. A method of treating atherosclerosis by inhibiting cholesterol biosynthesis comprising administering to a mammal in need of such treatment an amount effective for inhibiting cholesterol biosynthesis of a compound of the formula:

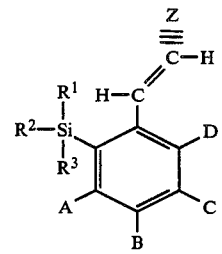

wherein each of $R^1$, $R^2$ and $R^3$ is independently, alkyl having from 1 to 4 carbon atoms; or phenyl which may be unsubstituted or substituted either by one or two alkyl or alkoxy groups having from 1 to 3 carbon atoms, or chloro; or by one fluoro, bromo or trifluoromethyl substituent;

A is a hydrogen atom or alkyl having from 1 to 3 carbon atoms,

B is a hydrogen atom; alkyl or alkoxy having from 1 to 4 carbon atoms; halo having an atomic weight of from about 19 to 80, trifluoromethyl; or phenyl, benzyl, or benzyloxy, wherein the aromatic portion may be unsubstituted, or substituted by one or two groups, one of which may be fluoro, bromo or trifluoromethyl; or one or two of which may be alkyl or alkoxy having from 1 to 4 carbon atoms, or chloro;

C is a hydrogen atom, alkyl or alkoxy having from 1 to 4 carbon atoms, halo having an atomic weight of from about 19 to 80, or trifluoromethyl; and D is a hydrogen atom, alkyl or alkoxy having from 1 to 4 carbon atoms, halo having an atomic weight of from 19 to 80 or trifluoromethyl;

and any of A+B, B+C, or C+D may constitute a 4 carbon radical of the formula R°; which is either $R^{°1}$:

—CH=CH—CH=CH—; or $R^{°2}$:

—(CH$_2$)$_4$—; with the provisions that the ring formed by the radical R° may bear one halo having an atomic weight of from about 19 to 80, or alkyl or alkoxy substituent having from 1 to 4 carbon atoms; and Z is a radical of the formula Z':

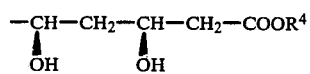

or a radical of the formula Z":

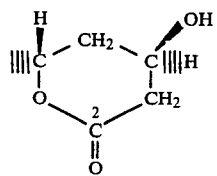

wherein $R^4$ is hydrogen, $C_{1-4}$alkyl, or benzyl; or M; wherein M is a cation forming a pharmaceutically acceptable salt:

with the provisions that there be no more than one trifluoromethyl group and no more than two bromos present on the molecule.

22. The compound of claim 1 which is the sodium salt of 3,5-dihydroxy-7-[2-(methyldiphenylsilyl)-6-methylphenyl]-6-heptenoic acid (erythro, trans).

* * * * *